United States Patent [19]
Akahane

[11] 3,961,448
[45] June 8, 1976

[54] WHOLE SPHERICAL SURFACE POLISHING DEVICE

[76] Inventor: Shoichi Akahane, No. 2192-2, Oaza Hiraide, Tatsuno, Kami-ina, Nagano, Japan

[22] Filed: Sept. 12, 1974

[21] Appl. No.: 505,381

[30] Foreign Application Priority Data
Dec. 12, 1973 Japan.............................. 48-139390

[52] U.S. Cl. .............................. 51/117; 51/289 S
[51] Int. Cl.² ........................................ B24B 11/10
[58] Field of Search ................. 51/289 S, 284, 154, 51/117, 71, 118

[56] References Cited
UNITED STATES PATENTS

| | | | |
|---|---|---|---|
| 1,806,918 | 5/1931 | Riggs | 51/289 S X |
| 2,352,178 | 6/1944 | Bolsey | 51/284 |
| 2,600,815 | 6/1952 | Turner | 51/284 X |
| 3,024,578 | 3/1962 | Mushkin | 51/289 S X |
| 3,111,789 | 11/1963 | Harmon | 51/289 S X |
| 3,133,383 | 5/1964 | Chapman | 51/289 S X |
| 3,577,690 | 5/1971 | Catron | 51/284 |

*Primary Examiner*—Donald G. Kelly
*Attorney, Agent, or Firm*—Michael J. Striker

[57] ABSTRACT

This invention relates to a polishing device which may polish the surface of a hard body such as metal, rock, glass or hard plastics into a perfect spherical shape. Each polishing device may also be applied for the mass-production of lenses, concave and convex. The polishing device comprises three identical polishing dishes mounted on the front ends of three rotating shafts which are positioned on three lines radiating from one point on a plane with an angular interval of 120°, respectively. Said polishing dish has a concave polishing surface and the three polishing dishes are adapted to support a body to be polished at the center of the device and to rotate in contact with the body. Therefore, it may be polished into a perfectly spherical shape.

5 Claims, 7 Drawing Figures

WHOLE SPHERICAL SURFACE POLISHING DEVICE

This invention relates to a polishing device which may polish the whole surface of a hard body such as metal, rock, glass or hard plastics into a perfect spherical shape.

One object of this invention is to provide a polishing device which may perform polishing of the whole spherical surface by one operation.

Another object of this invention is to provide a polishing device which may polish simultaneously plural pieces of lens material in a required curvature, concave or convex.

Further another object of this invention is to provide a polishing device which adjustment is easy to save labour during operation.

Heretofore, in polishing a body of hard material to provide a spherical surface thereto, it has been the practice to polish the upper half part of it by rotation of a polishing dish having a concave hemi-spherical surface while holding the lower part thereof. Since one operation can cover only less than a half of the whole spherical surface, it takes at least three operations to finish the whole of it. In the production of lenses, Oscar's process has been adopted as a polishing process to polish a lens to a required curvature. This process employes two molds, upper and lower. Plural pieces of lens material are attached to the lower mold which has a convex hemi-sphere, and the upper mold which is a polishing dish is rotated to perform a polishing operation. It will be understood that the surface area of the lower mold to which the pieces can be attached is substantially less than that of the hemisphere.

This invention differs from the conventional polishing process in the polishing mechanism. Briefly stated in accordance with this invention, there is provided a whole spherical surface polishing device comprising three identical polishing dishes which connect with three rotating shafts. The three rotating shafts are positioned along three lines radiating from one point on a plane, namely the center of the device, with an angular interval of 120°, respectively, and are journaled in bearings for rotation and for movement in the three axial directions of said three shafts, respectively. The polishing dish comprises a circular brim, a concave dish surface and a dish holder. The concave dish surface has a sectional arc of less than a central angle of 120°. Said three polishing dishes locate at an equal distance from the center of the device and are connected with the front ends of said rotating shafts. Said polishing dishes are adapted to rotate with said rotating shafts, and one among said three polishing dishes is fixed to one rotating shaft and two among said three polishing dishes are adapted to swing slightly at the front ends of said shafts as a center. An article to be processed is supported by said three dishes by the pressure in the three converging directions and can be polished by said dishes in rotation of said shafts. The rotation rates of the three rotating shafts need to have slight differences among them, respectively. Thereby, the article rotates while varying perpetually the direction of rotation thereof. Therefore, it suffers uniform polishing over the whole surface thereof and can be polished into a perfect spherical shape.

This invention will be better understood and other objects and additional advantages of the invention will become apparent upon perusal of the following description taken in connection with drawings, in which.

Referring more particularly the drawings, this invention will now be described; however, this description will be understood to be illustrative of the invention and not as limiting it to the particular construction shown and described.

Figure 1:
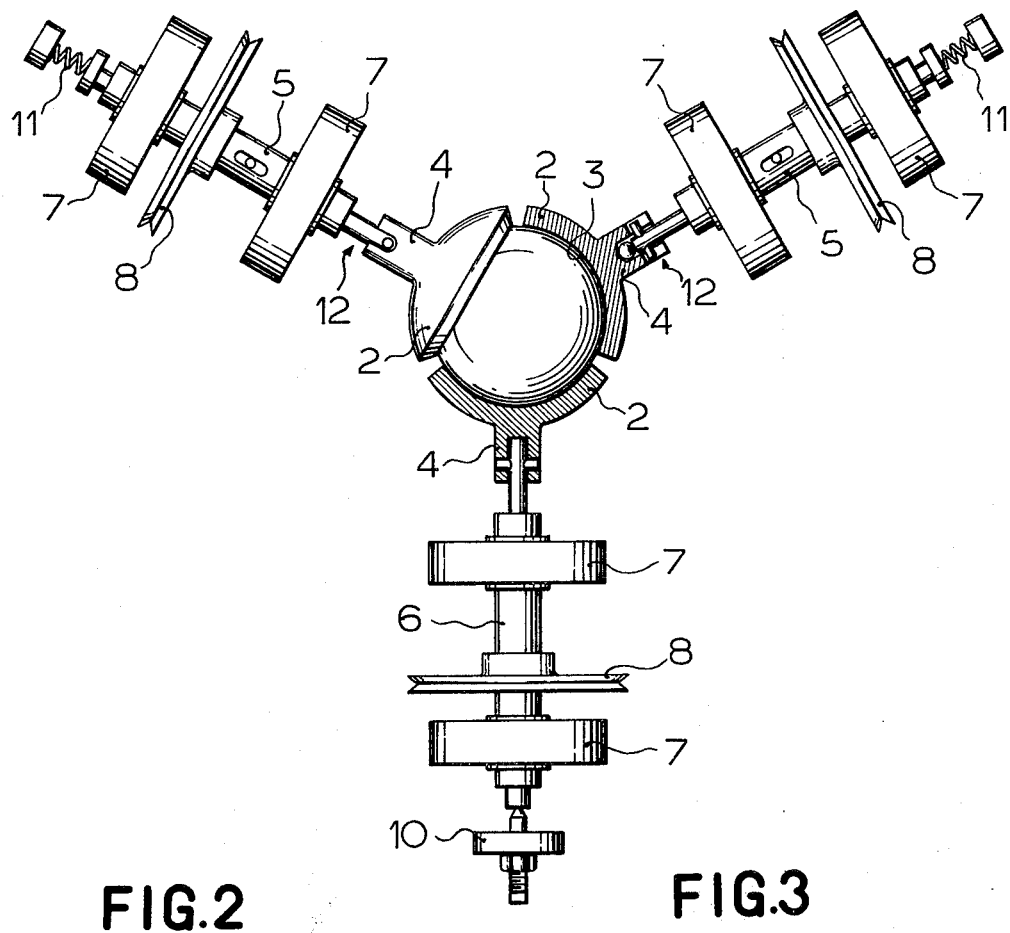
FIG. 1 is a partially sectional explanatory plan view of a whole spherical surface polishing device.
Figure 2:
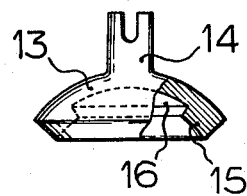
FIG. 2 is a partially sectional elevational view of an improved polishing dish.
Figure 3:
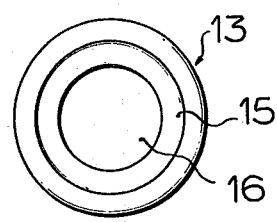
FIG. 3 is a plan view of a dish surface of the improved polishing dish.
Figure 4:
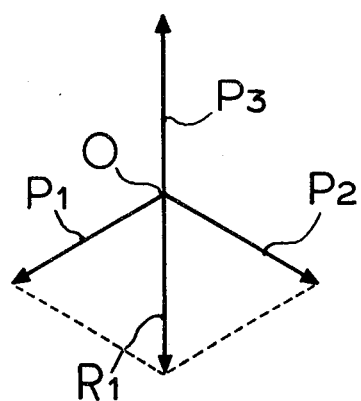
FIG. 4 is a diagram which shows the resultant of three angular velocities of the rotating shafts in the vector in the case of three equal rotation rates.
Figure 5:
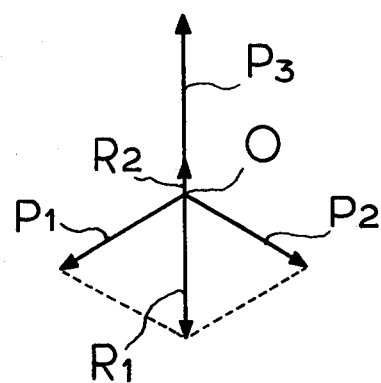
FIG. 5 is a diagram which shows the resultant of three angular velocities of the rotation shafts in the vector in the case of two equal rotation rates and one different rotation rate.
Figure 6:
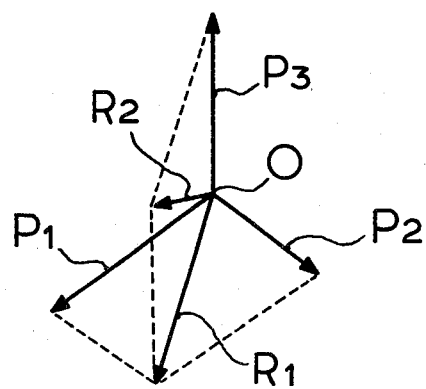
FIG. 6 is a diagram which shows the resultant of three angular velocities of the rotating shafts in the vector in the case of three different rotation rates.
Figure 7:
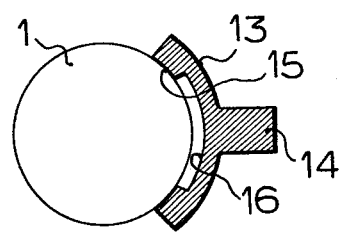
FIG. 7 is an explanatory view which shows the contact of the spherical body and the improved polishing dish.

The three rotating shafts 5, 5 and 6 are positioned along three lines radiating one point on a plane which is the center of the polishing device at an angular interval of 120° each other and three identical polishing dishes or lopping cups 2, 2 and 2 are mounted to the front ends of the shafts 5, 5 and 6 so as to be located at an equal distance from the center of the device. The rotating shafts 5, 5 and 6 are journaled in bearings 7 for rotation and made to move in the axial directions, respectively. The three polishing dishes 2, 2 and 2 bear and press an article 1 to be processed from the three directions so as to place the center of the article 1 right on the converging point of the three radiating lines. By rotation of the three rotating shafts 5, 5 and 6 with different rates, respectively, the polishing dishes 2, 2 and 2 rotate correspondingly with the varied rates, respectively, whereby the article 1 suffers uniform polishing over the whole surface and it is polished into a perfect spherical surface. In this invention, the difference of the rotation rates of the rotating shafts 5, 5 and 6 plays an important part which theoretical explanation will be made as follows. Polishing is performed by friction velocity between the contact surfaces of two bodies. Firstly, the conventional polishing process of a spherical surface is studied while comparing with the invention. When a body to be polished is held in the state of repose and another body namely a polishing dish rotates about a fixed axis while the two bodies keep in touch, the contact surfaces of the both bodies leave a dead point namely a point of zero in the friction velocity at the center of the rotation and the friction velocity becomes as larger at a spot as the distance of said spot is farther from the center. Therefore, it will be hardly possible to process an article so as to provide a perfect spherical surface in this manner. Nor is it easy to cause the rotating shaft to swing so as to eliminate the dead point of the friction velocity. According to this invention, three axial lines of the rotating shafts converge at one point with an angular interval of 120°, respectively, and the rotation of these shafts bestow the rotation to the processed article by the three polishing dishes. It is considered that there are three cases which explanation will be made with reference to FIGS. 4, 5 and 6, respectively. Here the angular velocities of the rotating shafts are expressed in the vectors of $P_1$, $P_2$ and $P_3$, respectively, with the angular velocity resultant from $P_1$ and $P_2$ being denoted as $R_1$ and the angular velocity resultant from $P_1$, $P_2$ and $P_3$ denoted as $R_2$. FIG. 4 shows the case where the rotation rates of the three shafts are equal. $R_1$ and $P_3$ are opposite in direction but equal to value. Therefore, $R_2$ becomes zero. In this case, the article 1 to be processed does not rotates and accordingly it has three dead points in polishing. FIG. 5 shows the case where two shafts have equal rotation rate. The resultant $R_1$ is equal to $P_1$ or $P_2$ in value and opposite to $P_3$ in direction. Therefore, $R_2$ is equivalent to the difference between $P_2$ and $R_1$ in value and its axis of rotation is identical with that of $P_3$. Here the article to be processed rotates about the axis of one shaft, therefore one dead point exists on the surface right at the rotation axis. In the case of FIG. 6, the rotation rates of the three shafts are different from each other, and $R_2$ is different from $P_1$, $P_2$ and $P_3$ in direction. Therefore, in this case no dead point exists on the surface of the article in polishing. But the article to be processed will theoretically rotate about the fixed axis of $R_2$. Accordingly it is considered that the polishing would not be performed with uniformity. As a matter of fact, however, the article is not of perfectly spherical shape at the beginning. Therefore, variations in the friction force between the polishing dishes and the article to be processed take place unceasingly. In addition, abrasion resulted from polishing produces variation in the pressure to the article. These factors exert an effect upon the resultant angular velocity $R_2$, whereby the rotation axis of $R_2$ varies continuously with its locus taking the form of endless or infinite locus. As a result, the surface of the article will suffer utterly uniform polishing. Thus a perfectly spherical surface can be obtained on it by only one operation. Concerning the connection of each of the rotating shafts 5, 5 and 6 and each of the corresponding polishing dishes 2, 2 and 2, the one polishing dish 2 is fixed to the front end of the rotating shaft 6 by a holder 4 of said dish 2 and the other two polishing dishes 2 and 2 are connected with the front ends of the other two rotating shafts 5 and 5 by ball joints 12 in the holders 4. The rotating shaft 6 to which the polishing dish 2 is fixed is provided with an adjusting screw 10 at the rear end of it to adjust the position of said shaft 6. The rotating shafts 5 and 5 which connect with the polishing dishes 2 and 2 by the ball joints 12 and 12 are provided with compression springs 11 and 11 at the rear ends of said shafts 5 and 5 to press them toward the center. The three polishing dishes 2, 2 and 2 support and press the article 1 to be processed which is placed with its center right on the converging point of the three axes of said shafts 5, 5 and 6. The rotation rates of the rotating shafts 5, 5 and 6 may be determined according to the kind of material and the spherical diameter of an article to be processed. In any case, as stated above, it is necessary that there should be slight differences of the rotation rates between the three shafts 5, 5 and 6, respectively. In actual polishing operation, suitable abrasives and rotation rates depend upon the material of the article. For example, in polishing an article which has a hardness of 6° and a diameter of 5 to 7 cm, the proper rotation rates will be 200 to 220 per minute. Said conditions for polishing, however, may be easily determined by experiences of the operator.

As described above, the whole spherical surface polishing device of this invention can efficiently provide a perfectly spherical surface to a body of any hard material. As further applications, this device can polish plural pieces of lens material attached to a spherical body which is placed at the center of the device, whereby a plurality of lenses having the same convex curvature can be produced at one operation. Still further, it is also possible to polish the concave surface by attaching plural pieces of lens material on the dish surfaces of the three polishing dishes and by placing a polishing body having a spherical shape at the center of the device. Thus, this invention may be applied for the mass production of lenses, concave and convex.

As described above, the polishing device of a new and useful type with great utilities and wide ranges of application is provided by this invention.

This invention becomes more efficient and more useful by improving the polishing dish described above. An improved polishing dish is different from the initial polishing dish in respect of the dish surface, namely the improved dish surface comprises an annular contact surface along the circular brim of the polishing dish and a circular non-contact hollow inside said annulus. The comparison of the initial and the improved polishing dishes will be discussed as follows. Assuming that an article to be processed is fixed and an initial polishing dish rotates about a fixed axis, each spot on the dish surface has a circular velocity in proportion to the distance from the axis to said spot. Therefore, the circular velocity is zero at the axis and is maximum at the brim of the polishing dish. Accordingly, the polishing action of each spot of the dish surface is also proportional to the distance from the axis to said spot. Namely, a spot about the brim of the dish surface has a maximum polishing action and the center of it has a zero polishing action. Since the polishing is the abrasion, the dish surface of the initial polishing dish is worn away in proportion to the distance from the center to each spot of said surface. Therefore, the curvature of the polishing dish becomes larger in the concave contact surface. In contrast to the polishing dish, the article becomes smaller in diameter of the sphere from abrasion of the spherical surface. From this fact, it is considered that the contact pressure between the dish and the article becomes uneven and stronger in nearness to the rotation axis of a zero circular velocity and the polishing action is consequently reduced during operation. For dissolving the above inconvenience, the contact surface of the polishing dish is modified hereinbefore. Since the contact surface of the improved polishing dish is the annular portion along the circular brim of the dish surface and a circular hollow portion of it is not a contact surface, polishing is uniformly performed over the article with a nearly equal circular velocity at each spot on the contact surface of said dish. During operation, the spherical radius of the article and the curvature of the polishing dish surface are permanently maintained to coincide with each other and a contact pressure to the article is permanently uniform. It is preferable that the width of the annulus of the contact surface is equal to one-eighth to one-fourth of the arc of 120° center angle of the sphere. The efficiency of polishing is much increased by using the improved polishing dish in this invention.

What I claim is:

1. Apparatus for lapping a complete spherical surface on a body in one operation, comprising three shafts located in a plane and having axes intersecting at one point in said plane and being angularly displaced from each other by angles of 120°; three lapping cups mounted at one of the ends of said shaft at equal distances from said point, each of said cups having a spherical contact surface adapted to contact the body to be processed through an angle of less than 120°, said cups being respectively connected to said shafts for rotation therewith and one of said cups being immovably fixed to one of said shafts and the other cups being respectively connected to the other two shafts for a slight tilting movement about said one end; bearing means mounting said shafts for rotation and for movement in axial direction; biasing means connected to said other two shafts for urging said other two shafts and the cups connected thereto towards said point; means engaging the other end of said one shaft for adjusting the axial position thereof; and drive means connected to each of said shafts for driving the same respectively at different speeds of rotation so as to revolve a body contacted by said spherical contact surfaces and to lap the whole surface of said body to a perfect spherical shape.

2. Apparatus as defined in claim 1, wherein said other two cups are mounted on the respective ends of said other two shafts by ball joints.

3. Apparatus as defined in claim 1, wherein said means engaging said other end of said one shaft comprises a set screw coaxial with said one shaft.

4. Apparatus as defined in claim 1, wherein said biasing means comprise compression springs respectively engaging the other ends of said other two shafts.

5. Apparatus as defined in claim 1, wherein said spherical contact surface of each cup is provided with a central depression so as to contact the body only with a spherical zone.

* * * * *